United States Patent [19]
Helenowski

[11] Patent Number: 5,531,673
[45] Date of Patent: Jul. 2, 1996

[54] VENTRICULAR CATHETER

[76] Inventor: Tomasz K. Helenowski, 936 Burnham Ct., Glenview, Ill. 60025-4140

[21] Appl. No.: 452,015

[22] Filed: May 26, 1995

[51] Int. Cl.⁶ .................................................. A61M 5/00
[52] U.S. Cl. .................. 604/9; 604/275; 604/280
[58] Field of Search ........................ 604/902, 266, 604/267, 275, 280, 9

[56] References Cited

U.S. PATENT DOCUMENTS

| | | | |
|---|---|---|---|
| 3,109,429 | 11/1963 | Schwartz | 604/9 |
| 4,398,910 | 8/1983 | Blake et al. | 604/266 |
| 4,465,481 | 8/1984 | Blake | 604/280 |
| 4,885,002 | 12/1989 | Watanabe et al. | 604/9 |
| 4,990,133 | 2/1991 | Solazzo | 604/280 |
| 5,071,412 | 12/1991 | Noda | 604/268 |
| 5,078,714 | 1/1992 | Katims | 604/280 |
| 5,116,310 | 5/1992 | Seder et al. | 604/266 |
| 5,201,723 | 4/1993 | Quinn | 604/280 |
| 5,385,548 | 1/1995 | Williams | 604/280 |

FOREIGN PATENT DOCUMENTS 1662582  7/1991  U.S.S.R. ................. 604/280

*Primary Examiner*—Michael J. Milano

[57] ABSTRACT

A tubular ventricular catheter having an improved distal open end that improves the fluid flow therein and which reduces the tearing of any choroid plexus or other brain tissue which might grow into the lumen of the catheter. The catheter tip is provided with longitudinal slots extending from the distal end and partially through the elongated body of the catheter. To preserve the open communication of the tip to fluid flow the edges of the longitudinal slots can be scalloped by a series of semicircular cutouts, which will form lateral passageways into the center bore of the catheter in the event the distal open end collapses. The catheter is also equipped with an electrical signal generator which will function to prevent growth of tissue into the lumen, and aid in proper placement of the proximal end of the catheter in the ventricle.

7 Claims, 2 Drawing Sheets

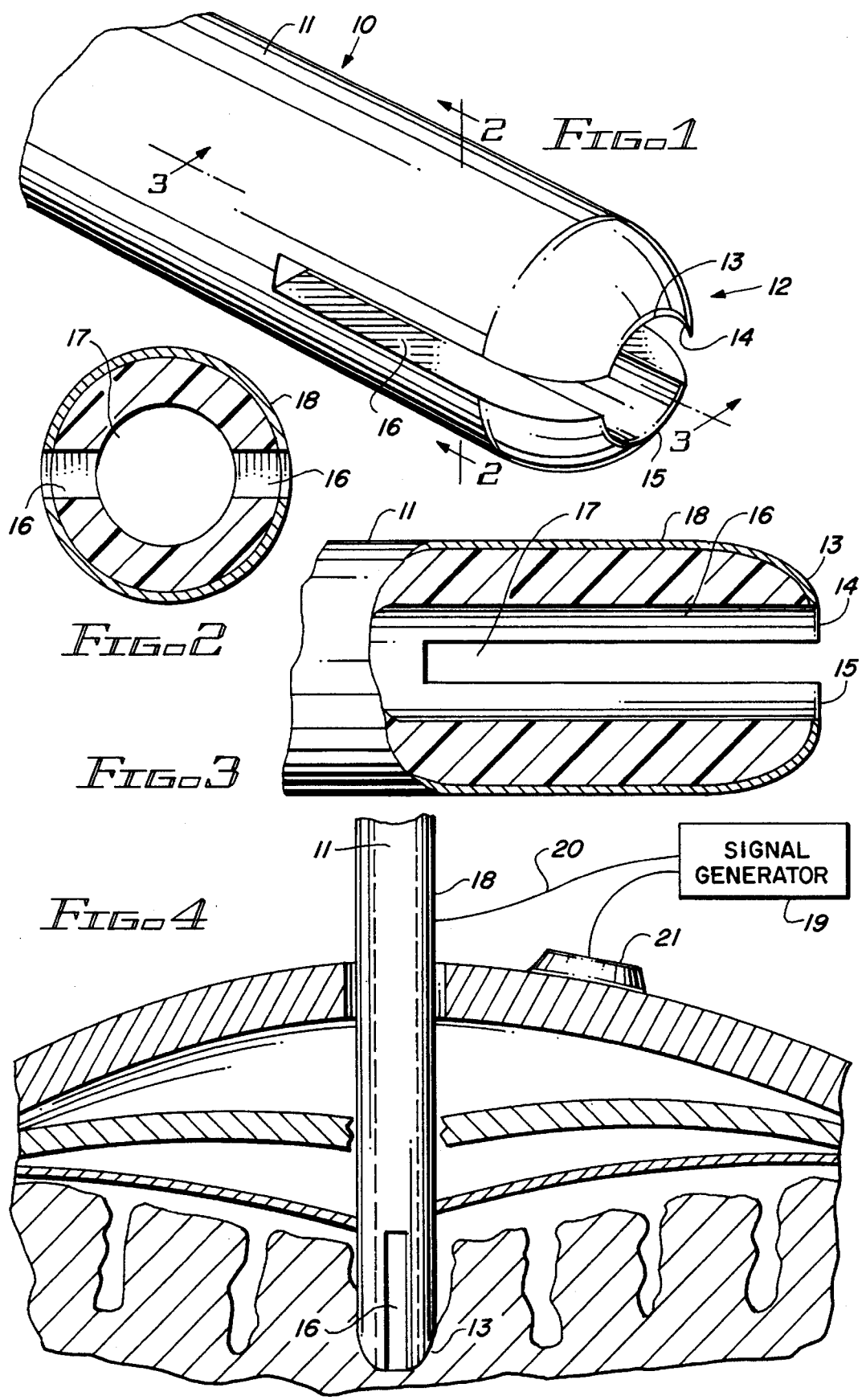

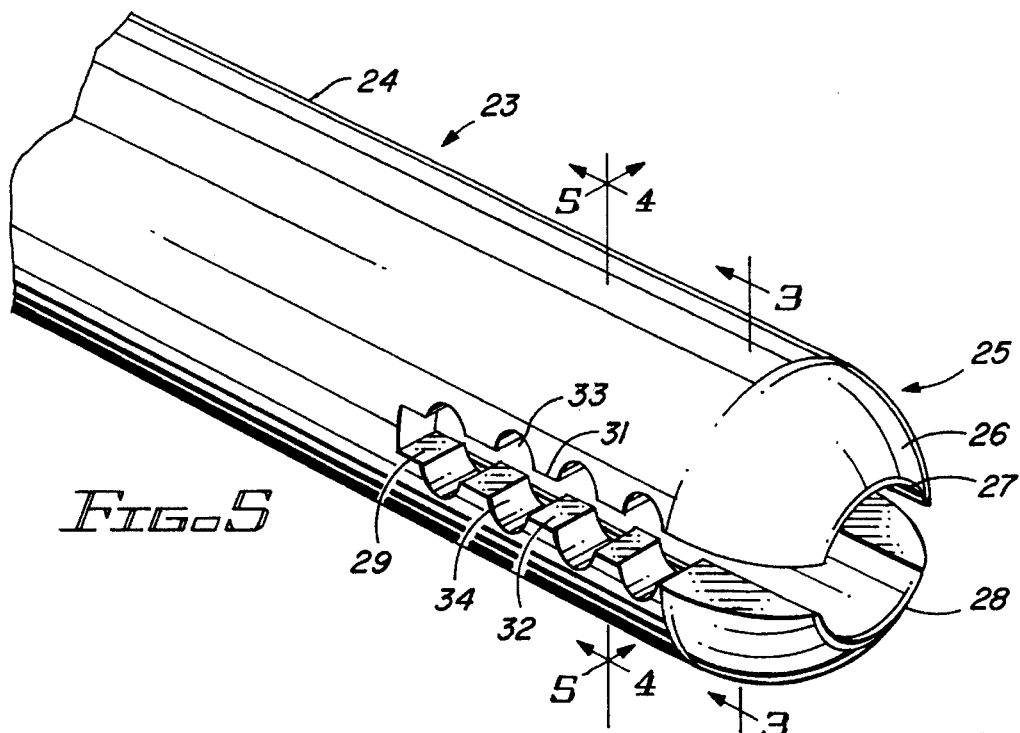
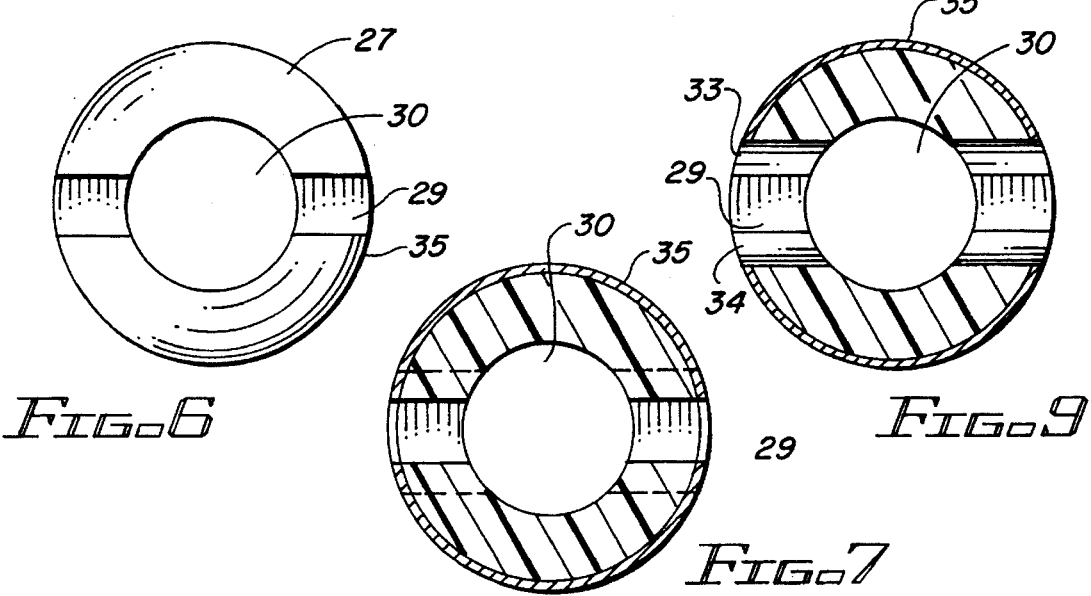
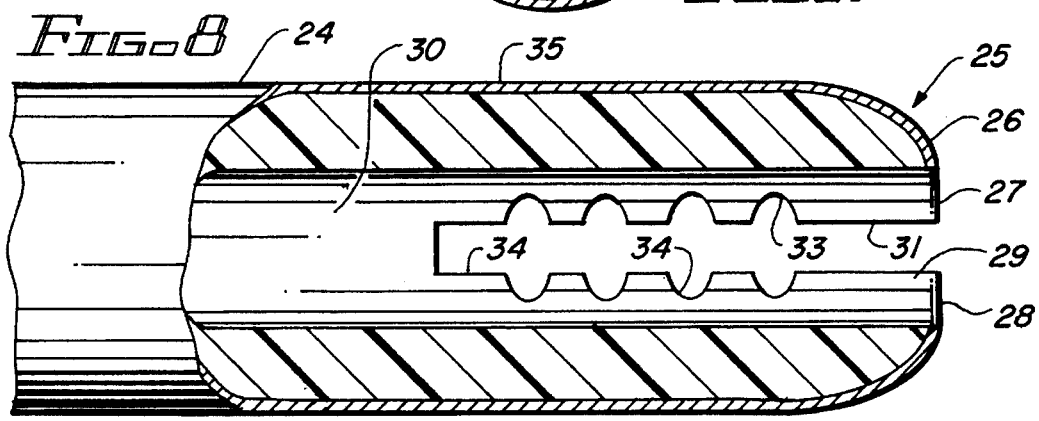

VENTRICULAR CATHETER

FIELD OF INVENTION

Hydrocephalus is a condition in which there is an excess build-up of fluid in the cranial vault. The increase fluids causes pressure on the brain and/or stretching of the brain structures. This pressure and stretching can cause malfunction of neural tissue and symptoms which are normally related to hydrocephalus.

The treatment of hydrocephalus is usually accomplished by the surgical placement of cerebrospinal fluid shunts. Shunts are mechanical systems of valves and tubes which divert the flow of the fluid either out of the cranial cavity or into the sub-arachnoid space where the fluid can be absorbed. The proximal end of the system is usually placed in cavities of the brain called ventricles. Most of the times this drainage is directed into the peritoneal cavity (ventriculo-peritoneal shunts or VPS) or the heart (ventriculo-atrial shunts or VAS ). Other sites of the proximal and distal ends are possible but constitute the majority of the cases.

During the use of cerebrospinal fluid shunts brain tissue tends to grow into the proximal end of the shunt tubing thereby obstructing the openings and causing the system to fail. The repair of the system requires surgery which has its risks, including bleeding, infection, and anesthetic complications.

The bleeding is caused when the tissue is torn by the proximal tip of the catheter as it is withdrawn. To reduce the chance of tearing this tissue, a new catheter tip is employed.

Prior devices, because of their design were ineffective, in that the open proximal end of the catheter element tended to become clogged by suctioned tissue as well as normal tissue growth which during prolonged penetration clogged the open end disrupted the fluid shunt.

In an attempt to overcome the clogging problem the prior art relied on controls for the suction/vacuum flow.

SUMMARY OF THE INVENTION

The ventricular tip of present shunt systems is usually made of a sealed piece of silicone tubing. A series of holes are punched in the sides of the tubing toward its sealed end. The fluid flows through these holes into the lumen of the tubing. When the choroid plexus, or other brain tissue grows into the holes it tends to bridge in the lumen of the tubing. When the lumen of the tube is completely obstructed, surgery is needed to replace the ventricular catheter or attempts must be made to clear its tip of this tissue. To accomplish the revision, the catheter is usually removed from the ventricle by pulling it out, with resulting tearing of the tissues, which tends to cause bleeding in the fluid space surrounding the brain.

To alleviate the bleeding caused when the tissue is torn by the proximal tip of the catheter when it is withdrawn a new catheter tip has been devised. This tip has a rounded open end, with two longitudinal slots cut in the side wall that extends partially through the length of the catheter. If tissue grows into these slots and causes an obstruction to the flow of fluid therethrough, the tissue does not have to be torn to remove the catheter, the catheter tip simply slips out of the tissue.

To aid in achieving the objects of this invention the proximal tip of the catheter can have the elongated confronting walls which define the slots scalloped by a series of semi-circular cutouts, juxtaposed to form lateral passageways in communication with the lumen of the catheter. In the event the proximal tip of the catheter becomes clogged or collapses under the growth of the surrounding tissue, these passageways will remain open and permit the shunt to continue to function.

One of the ways cells communicate with themselves is by the use of electrical signals. Manufactured electrical signals have been used in the treatment of bone fractures which do not heal. Electrodes are implanted and a low current is applied to the tissues to promote faster healing. To achieve the opposite i.e. the discouragement of tissue growth a opposite charged electrode can be placed in a distal location and tissue healing or growth will not occur around it. In the shunt system, this opposite electrode can be present in the ventricular catheter to prevent growth of tissue into the lumen. The electrode can consist of any conductor, either inserted into, or applied as a coating on the catheter. By preventing growth of new tissue, shunt malfunctions can be greatly reduced and obviate the need for repeated surgical procedures. The electrical signal can be produced by a battery operated generator which is part of the shunt system.

Other objects of the present invention are hereinafter made apparent.

DESCRIPTION OF THE DRAWINGS

The invention will be best understood by reference to the accompanying drawings which illustrates the preferred form of construction and arrangement of parts by which the objects of the invention are achieved and in which:

FIG. 1 is a fragmentary perspective view of the ventricular catheter of this invention, FIG. 2 is a detailed sectional view of the catheter tip taken on line 2—2 of FIG. 1, FIG. 3 is a fragmentary detailed sectional view of the catheter tip taken on line 3—3 of FIG. 1, FIG. 4 is a schematic view of the catheter tip of this invention positioned within the cranial vault, FIG. 5 is a fragmentary perspective view of a modified ventricular catheter tip, FIG. 6 is a is an end view of the catheter tip of FIG. 5, FIG. 7 is a detailed sectional view taken on line 3—3 of FIG. 5, FIG. 8 is a fragmentary detailed sectional view taken on line 5—5 of FIG. 5 and FIG. 9 is fragmentary sectional view taken on line 4—4 of FIG. 5.

DESCRIPTION OF THE INVENTION

The ventricular catheter tip 10 of this invention is illustrated in FIG. 1 wherein it is shown that the tip 10 consists of a elongated tubular body 11 which provides a reduced rounded tip 12 terminating into a nose 13 formed from spaced apart arcuated segments 14 and 15.

The tubular body 11 of the tip 10 is provided with longitudinally slots 16 extending parallel to the longitudinal axis of the body 11 and in open communication with its lumen 17. The slots 16 are also cut into the rounded tip 12 and through the nose 13 of the tip as shown.

The entire outer surface of the catheter 10 is coated with an electrical conductive material 18. A low level electrical signal generator 19 maybe suitably associated with the coating 18 through an external conductor 20 as illustrated in FIG. 4.

The purpose of the electrical conductive coating 18, in association with the signal generator 19, is to produce an electrical signal at the proximal end of the catheter to discourage tissue growth into the lumen 17. The opposite electrode 21 of the signal generator 19 can be grounded as at 22 at a distal location from the catheter tip 10.

The electrode consisting of the conductive coating 18 can be replaced by any other type of conductor which can be carried by or inserted into the catheter tip 10. As for example the cerebrospinal fluid as contained within the lumen 17 of the body 11 can constitute an electrical signal conductor.

By preventing growth of new tissues, shunt malfunctions can be greatly reduced, and obviate the need for repeated surgical procedures. The electrical signal can be produced by a battery operated signal generator which can be part of the shunt system.

Referring to FIG. 5 a modified ventricular catheter tip 23 is illustrated and it consists of an elongated tubular body 24 which provides a reduced rounded tip 25 terminating into a nose 26 formed from spaced apart arcuated segments 27 and 28. The longitudinal slots 29 cut in the walls of the tip, are in open communication with the body's lumen 30 and extend through the rounded tip 24 as shown, The confronting longitudinal walls 31 and 32 of each of the slots 29 are scalloped by a series of semi-circular cutouts 33 and 34 which are juxtaposed with respect to each other. In the event that the nose 26 becomes clogged or collapses under the pressure of tissue growth the laterally extending semi-circular cutouts 33 and 34 will mate and provide open communication with the lumen 30.

The modified catheter tip 23 can also be coated with a conductive material 35 for the purpose herebefore described.

Insertion of the ventricular catheter to the appropriate depth of the brain cavities or ventricles determines to a large degree whether or not the shunt will function properly. If the tip of the shunt is inserted to deep the lumen can become plugged when the ventricles decrease in size. The conductively coupled tip on the ventricular catheter can determine when its tip is in cerebrospinal fluid and when it is contacting brain tissue at its tip. This determination can be made by measuring the electrical impedance from a ground on the patients body to the catheter tip. Thus the catheter can be inserted for optimal positioning.

From the foregoing it is apparent that there has been described a new ventricular catheter which possesses rounded open tip which is slotted for improved fluid flow and one which reduces the chance of tearing tissue as the shunt tip is withdrawn from the ventricle. The longitudinal slots formed in the catheter tip can be scalloped by means of a plurality of semi-circular cutouts formed in the elongated walls which define the slots. The catheter is also provided with a conductive path to send signals to prevent tissue from growing into the catheter and clogging its lumen and thus preventing fluid flow there through.

While I have illustrated the preferred form of construction for carrying my invention into effect, this is capable of variation and modification without departing from the spirit of the invention. I therefore, do not wish to be limited to the precise details of construction as set forth, but desire to avail myself of such variations and modification as come within the scope of the appended claims.

Having thus described my invention what I claim as new and novel and desire to protect by letters patent is:

1. A ventricular catheter adapted to be incorporated into a fluid shunt system comprising:

a) an elongated tubular body providing an open rounded end, b) means extending from said rounded end and partially through the longitudinal length of said body providing open communication with the lumen thereof through which cerebrospinal fluid is shunted, and c) a low level electrical signal generator, and means for transmitting a signal therefrom to said tubular body to restrict growth of choroid plexus or other brain tissue into the lumen of the catheter.

2. A ventricular catheter as defined by claim 1 wherein said means extending from said rounded end and partially through the length of said body for providing open communication with the lumen thereof comprises parallelly extending slots.

3. A ventricular catheter as defined by claim 1 wherein said means for transmitting a signal to said tubular body consists of a conductive coating.

4. A ventricular catheter as defined by claim 2 wherein said means for transmitting a signal to said tubular body consists of a conductive coating.

5. A ventricular catheter adapted to be incorporated into a fluid shunt system comprising:

a) an elongated tubular body providing an open rounded end, b) first means extending from said rounded end and partially through the longitudinal length of said body providing open communication with the lumen thereof, and c) other means extending perpendicular to the longitudinal axis of said body and said first means providing open communication with the lumen of said body through which cerebrospinal fluid is shunted, and d) a low level electrical signal generator, and means for transmitting a signal therefrom to said tubular body to restrict growth of choroid plexus or other brain tissue into the lumen of the catheter.

6. A ventricular catheter as defined by claim 5 wherein said first means extending from said rounded end of said body comprises parallel slots, and said other means extending perpendicular to the longitudinal axis of said body and said first means comprises a series of semi-circular cutouts formed in the walls defining said slots.

7. A ventricular catheter as defined by claim 5 wherein said means for transmitting a signal to said tubular body consists of a conductive coating.

\* \* \* \* \*